United States Patent [19]

Wilde

[11] Patent Number: 4,986,108

[45] Date of Patent: Jan. 22, 1991

[54] AUTOMATIC MATERIAL ASSAY

[75] Inventor: Geoffrey Wilde, Bolton, England

[73] Assignee: Cargill UL Limited, London, England

[21] Appl. No.: 331,909

[22] Filed: Mar. 31, 1989

[30] Foreign Application Priority Data

Apr. 28, 1988 [GB] United Kingdom ............... 8810074

[51] Int. Cl.$^5$ ............................................. G01C 25/00
[52] U.S. Cl. .................................................... 73/1 R
[58] Field of Search ......................................... 73/1 R

[56] References Cited

U.S. PATENT DOCUMENTS

| | | | |
|---|---|---|---|
| 4,493,897 | 1/1985 | Tabara | 436/43 |
| 4,502,121 | 2/1985 | Clavier et al. | 324/324 |
| 4,581,935 | 4/1986 | Breazeale | 73/599 |
| 4,761,608 | 8/1988 | Franklin et al. | 73/1 J |
| 4,835,545 | 5/1989 | Mager et al. | 354/4 |
| 4,847,204 | 7/1989 | Mitzner et al. | 436/8 |

FOREIGN PATENT DOCUMENTS 54-54311 11/1980 Japan .

OTHER PUBLICATIONS

Kaza, Soviet Inventions Illustrated, week 8411, Apr. 25, 1984, SU-A-1029 621.

Primary Examiner—Robert Raevis
Attorney, Agent, or Firm—Pearne, Gordon, McCoy & Granger

[57] ABSTRACT

Material such as cotton is assayed using equipment that needs to be calibrated against a sacrificial standard which is itself subject to variation from sample to sample. The invention comprises using in the calibration an average standard sample value derived from a plurality of calibrations.

9 Claims, 1 Drawing Sheet

AUTOMATIC MATERIAL ASSAY

BACKGROUND TO THE INVENTION

This invention relates to assaying material properties.

In the automatic assay of cotton using HVI/HVT equipment it is necessary to calibrate the equipment periodically using a standard cotton sample prepared by a standards institute, namely the U.S. Department of Agriculture.

In order to perform an assay on a shipment of cotton, samples are taken from the shipment and subjected to the assay routines built into the HVI/HVT equipment, these routines including length, uniformity, strength and so on. For calibration purposes, the same routines are performed on the standard cotton supplied by the USDA. The equipment automatically adjusts its internal parameters (or in some older equipment those internal parameters may have to be manually adjusted) to correspond to the standard values of the sample, which are supplied by the USDA along with the sample.

This way of working, which, on the face of it appears to be perfectly rational, has been an internationally agreed—not to mention mandatory-procedure for some considerable period of time. The internationally recognised standard is controlled by the USDA and its sample cotton is ubiquitous. The importance of the assay procedure is that the price and often the suitability of the cotton is determined by it. Clearly, if the price is wrong, somebody loses something, which may be marginal; if the end use is wrong, the resulting loss may be substantially greater in that faulty goods may be very expensively produced wasting the entire batch of cotton.

In most testing houses, calibration is carried out at least once, often twice a day; in the USDA's testing establishment, calibration is carried out much more frequently in order to try to ensure the highest degree of accuracy.

The present invention is based on the problem that, notwithstanding the efforts made to ensure accuracy using the mandatory calibration procedure and the USDA standard sample, there is usually variable correlation between the assay results of different testing houses, and indeed usually, on an inter-house comparison basis, a significant number of testing houses (not, in different instances, the same houses) cannot differentiate between different standard samples, for example between standard strong and standard weak cottons.

This problem is usually ascribed to differences in operator procedures or techniques, differences in humidity and other uncontrollable or uncontrolled variables, and the concensus of opinion in the trade is that these problems are unavoidable.

However, we have now found that the problems do not reside in such areas as has hitherto been supposed, and we have also found that the problems are by no means unavoidable.

BRIEF DISCLOSURE OF THE INVENTION

The invention comprises a method for carrying out automatic assay of material properties using equipment that needs to be calibrated against a sacrificial standard which is itself subject to variation from sample to sample, comprising using in the calibration an average standard sample value derived from a plurality of calibrations.

The method may comprise using in the calibration an average standard sample value derived from as many calibrations as have been carried out on the equipment using a given batch of standard sample material The solution to the problem is based upon the realisation that, contrary to the prevailing view, the supposedly standard cotton itself exhibits surprising variation, which is not adequately compensated for even when basing the calibration on the average of tests on four samples of the standard cotton.

BRIEF DESCRIPTION OF THE DRAWINGS

The automatic assay method according to the invention will now be described with reference to the accompanying drawings, in which.

DETAILED DISCLOSURE OF THE PREFERRED EMBODIMENTS

Figure 1:
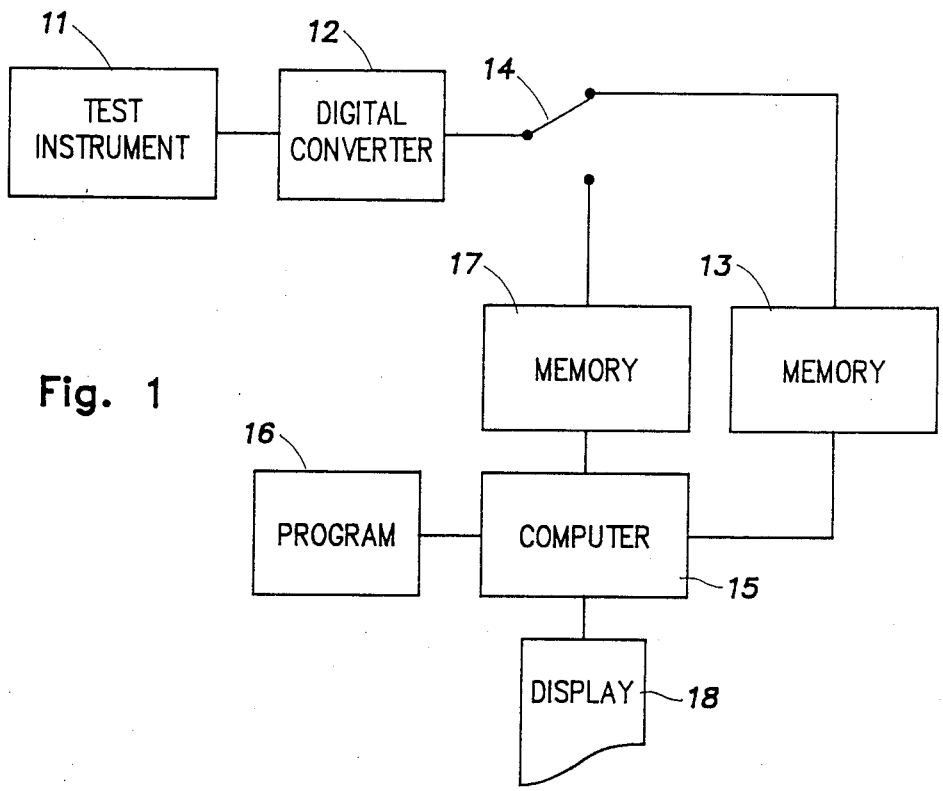
FIG. 1 is a diagrammatic illustration of an assay apparatus.

The apparatus illustrated in FIG. 1 comprises a test instrument 11, which might for example comprise an automated length measuring device which combs out a sample of fibres held in a clamp over a window through which light is shone on to a detector, the way light is obscured indicating the average length of the fibres; such an instrument might also be combined with a strength tester in which another clamp grips the fibres and applies a tensile force until they break. Or the test instrument might be a so-called micronaire tester in which the volume of a known mass of fibre is estimated by evacuating a chamber of known volume in which the mass is placed, the estimated volume being converted to an estimate of the average fibre diameter Such instrumentation is combined in a comprehensive cotton assay arrangement generally spoken of as an HVI line and such lines are to be found associated with cotton exchanges around the world.

The instrumentation is not regarded as an absolute measurement instrument rather as a comparator. For this reason a calibration arrangement is built in to the instrumentation.

An analogue signal from the test instrument 11 is converted to digital form in an analogue to digital converter 12 and for calibration purposes passed to a memory 13 by means of a calibration switch 14. In practice, four separate measurements of the same variable are carried out in a standard calibration procedure and the memory 13 has an associated computation that evaluates and stores the average and variance derived from the four measurements.

The calibration measurements are carried out on standard cotton produced as such by the USDA with known average and variance for each of the variables of interest.

If the results of the calibration procedure are within limits centred on the known values for the standard cotton, the instrument arrangement is deemed to be within calibration. If, however, the results are outside those limits, it is assumed that the instrumentation needs recalibrating and it is automatically recalibrated by the internal parameters being adjusted by programming in the arrangement.

The stored calibration measurements are evaluated in a computer 15 and compared with the standard values as supplied by the USDA which are input manually via the usual keyboard arrangement. If recalibration is called for the computer calls upon a parameter change program arrangement 16 (which might be embodied in software) which alters the parameters in the algorithms programmed into the computer 15 which calculate the average and variance of the results of assay measurement to be performed on cotton using the calibrated instrumentation.

Once calibrated, the calibration switch 14 is switched to run regular assay tests and the digital signals are fed into a store or memory 17 for subsequent evaluation by the computer 15. It is to be understood of course that the stores 13 and 17 may be contained in different memory locations of the same memory arrangement such as a magnetic disc or RAM associated with the computer 15.

The computed results are passed to a display arrangement 18 which may of course comprise a screen and/or printer as is conventional.

Calibration is normally carried out on a regular and frequent basis—always, for example, when the instrument is switched on at the start of the working day, and often, again, at the beginning of the afternoon. It is assumed that the electronics might be subject to drift, that humidity and other ambient conditions will affect the results and that different operators might influence the instrumentation differently.

Each time calibration is carried out, a fresh sample from a supply of standard cotton is used, of course, the standard cotton being thus sacrificial—once used in a strength test calibration, naturally, it cannot be used again.

Conventionally—indeed it is standard, mandatory practice—after each time the instrumentation is calibrated, the results of the previous calibration are lost.

According to the present invention, however, the results of all, or at least a larger number of, calibrations are saved (so that the calibration store 13 is necessarily a non-volatile store such for example as a magnetic store or a non-volatile RAM). By 'saved', of course, is not necessarily meant saved individually, rather that, in whatever fashion, a cumulative statistic is calculated based on all or a larger number of previous calibrations.

Figure 2:
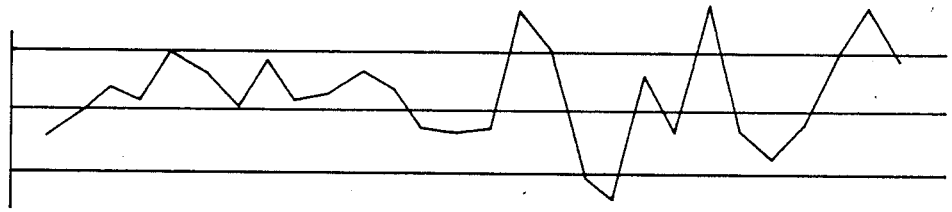
FIG. 2 is a graph showing the results of estimations of one variable based on the averages of sets of four measurements of a standard cotton sample supplied by USDA.

FIG. 2 is a graph of test results on calibration cotton supplied by the USDA. The variable tested and the scale are immaterial, but the results would be typical of length, strength or micronaire tests, say. Each point on the graph represents the average value of the four measurements.

Figure 3:
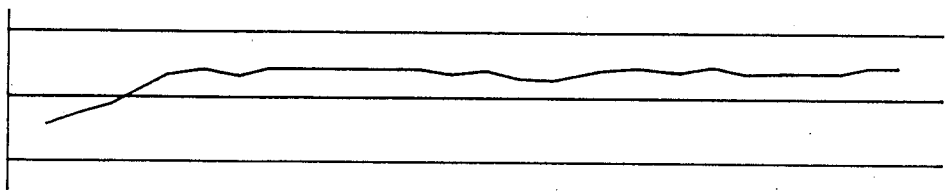
FIG. 3 is a graph like FIG. 2 but based on the cumulative results of sets of four measurements of the same variable.

FIG. 3 is a graph of the same test results but on a cumulative basis, whereby the individual test data is averaged together with all preceding test data to arrive at a cumulative average.

It will be seen that the FIG. 3 graph rapidly levels off to a reasonably constant value. It is now clear that this value is a much better statistic to use in the calibration than the non-cumulative averages of FIG. 2 which are, by comparison, all over the place and which require frequent adjustment of the parameters of the instrumentation against which market cotton is assayed. Such adjustments are now seen to be spurious and to be likely to give rise to erroneous assays.

Indeed, it can, on the basis of the foregoing, be argued that once a reasonable level value has been attained for the cumulative statistic of FIG. 3—and this seems to happen, as a practical matter, after some ten to fifteen results of four measurements each—further calibration procedure are pointless, and values of the various statistics based on the first ten to fifteen calibration procedures can be used thereafter.

This might, of course, overlook such factors as drift of the electronics, ambient conditions and operator idiosyncracies, but it now appears that by and large these factors are of minor significance, and have been erroneously blamed for erroneous results, now attributable to the standard calibration procedure.

However, there are various ways of proceeding based on the present invention which may be preferred in different circumstances.

One way is to run the calibration procedure using standard calibration cotton, on the same regular basis as at present, but 'saving' the results on a cumulative basis as indicated above.

Another way is to proceed as above but only until the calibration statistics have levelled out after say ten or fifteen calibration procedures have been run, then to discontinue the procedure thereafter relying on the levelled out values.

Another way is to run all ten or fifteen procedures at once on first commissioning the instrumentation, or whenever some major disturbance of the instrumentation occurs on repair or maintenance for example.

Another way is to run the procedure regularly as at present, having only the last ten or fifteen results on a moving cumulative basis as giving a better statistic than the conventional series of four tests in a single calibration procedure.

The choice from among these options may well depend upon details of the instrumentation, whether there is for example a real possibility of significant drift in electronic components, or whether wear and tear on mechanical parts needs to be monitored, whether, also, ambient conditions have a real rather than a supposed effect and so on.

It should be observed that two of the options result in significant savings of time, since calibration is virtually eliminated as a daily chore, and drastically reduce the amount of expensive calibration cotton required.

Whilst the invention has been described with particular reference to cotton assay, it would equally well apply in other cases where sacrificial calibration standard materials are used.

I claim:

1. A method of carrying out automatic assay of the material properties of a substance, said material properties being variable, using equipment that needs to be calibrated against a sacrificial standard which is itself subject to variation from sample to sample, comprising using in the calibration a cumulative average standard sample value derived from a cumulative plurality of calibrations.

2. A method according to claim 1, comprising using in the calibration an average standard sample value derived from as many calibrations as have been carried out on the equipment using a given batch of standard sample material.

3. A method to claim 1, in which the substance is textile fibers.

4. A method according to claim 3 in which the text fibre is cotton.

5. A method according to claim 1, in which the average standard sample value is derived from all calibrations on a cumulative basis.

6. A method according to claim 1, in which the average standard sample value is derived from an initial set of calibration procedures on a cumulative basis up to such time as the value levels out.

7. A method according to claim 6, in which all the calibration procedures are carried out on first commissioning a material testing instrumentation or whenever some major disturbance of said instrumentation occurs on repair or maintenance without any actual assay being carried out in between the calibrations.

8. A method according to claim 1, in which the average standard sample value is a moving average derived from a predetermined number of immediately preceding calibrations.

9. A method according to claim 1, in which the said plurality of calibrations is in the range 10-20.

* * * * *